United States Patent [19]

Gueremy et al.

[11] Patent Number: 4,613,607
[45] Date of Patent: Sep. 23, 1986

[54] MEDICAMENTS BASED ON DERIVATIVES OF 1-(4-QUINOLYL)-2-(4-PIPERIDYL)-ETHANOL OR 1-(4-QUINOLYL)-3-(4-PIPERIDYL)-PROPANOL

[75] Inventors: Claude G. A. Gueremy, Houilles; Michel A. P. Mestre, Paris; Christian L. A. Renault, Taverny, all of France

[73] Assignee: Pharmuka Laboratoires, Gennevilliers, France

[21] Appl. No.: 537,157

[22] Filed: Sep. 30, 1983

Related U.S. Application Data

[63] Continuation of Ser. No. 324,713, Nov. 24, 1981, abandoned.

[30] Foreign Application Priority Data

Dec. 5, 1980 [FR] France ................................ 80 25829

[51] Int. Cl.$^4$ ...................... A61K 31/47; C07D 215/14
[52] U.S. Cl. .................................... 514/314; 514/821; 546/173; 546/176; 546/177
[58] Field of Search ................ 546/176, 177; 424/258; 514/314, 821

[56] References Cited

U.S. PATENT DOCUMENTS

| | | | |
|---|---|---|---|
| 3,914,235 | 10/1975 | Gutzwiller et al. | 424/258 X |
| 3,953,453 | 4/1976 | Grethe et al. | 546/134 |
| 4,237,139 | 12/1980 | Champseix et al. | 424/258 |
| 4,402,961 | 9/1983 | Dubroeucq et al. | 424/258 |
| 4,405,789 | 9/1983 | Champseix et al. | 546/176 |
| 4,433,150 | 2/1984 | Champseix et al. | 546/168 |
| 4,442,106 | 4/1984 | Trijzelaar et al. | 424/258 |
| 4,442,107 | 4/1984 | Trijzelaar et al. | 424/258 |
| 4,443,453 | 4/1984 | Trijzelaar et al. | 424/258 |
| 4,472,403 | 9/1984 | Trijzelaar et al. | 424/258 |

FOREIGN PATENT DOCUMENTS

| | | | |
|---|---|---|---|
| 0030044 | 6/1981 | European Pat. Off. | 424/258 |
| 0031753 | 7/1981 | European Pat. Off. | 424/258 |
| 0035819 | 9/1981 | European Pat. Off. | |
| 0330813 | 12/1920 | Fed. Rep. of Germany . | |
| 2315148 | 10/1973 | Fed. Rep. of Germany | 546/176 |
| 2206944 | 6/1974 | France | 546/177 |
| 7908030 | 6/1981 | Netherlands . | |

OTHER PUBLICATIONS

Heidelberger, et al., J. Am. Chem. Soc., vol. 44, pp. 1098–1107 (1922).
Wirth, Chemical Abstracts, vol. 76, 103776f (1972).
Wirth, Chemical Abstracts, vol. 80, 124762w (1974).
Ainley, et al., Proceedings Royal Society (London) B 125, pp. 60–92 (1938).
Dawes, Brit. J. Pharmacol. 1, pp. 90–111 (1946).

*Primary Examiner*—Mark L. Berch
*Assistant Examiner*—Diana G. Rivers
*Attorney, Agent, or Firm*—Beveridge, Degrandi & Weilacher

[57] ABSTRACT

Antiarhythmic medicaments containing, as active substance, a compound of the formula:

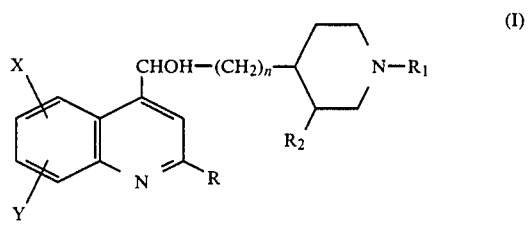

in which n is 1 or 2, X and Y are fixed in positions 5, 6, 7 or 8 on the quinoline cycle and each represents a hydrogen atom or an alkoxy group having 1 to 3 carbons, R is a hydrogen atom or an alkyl group having 1 to 4 carbons, cycloalkyl having 3 to 8 carbons, phenyl or phenyl substituted by alkoxy having 1 to 4 carbons, $R_1$ is a hydrogen atom or an alkyl group having 1 to 4 carbons or a phenylalkyl group of which the alkyl part has 1 to 3 carbons, $R_2$ is a hydrogen atom, an alkyl group having 1 to 2 carbons or an alkenyl group having 2 to 4 carbons.

21 Claims, No Drawings

MEDICAMENTS BASED ON DERIVATIVES OF 1-(4-QUINOLYL)-2-(4-PIPERIDYL)-ETHANOL OR 1-(4-QUINOLYL)-3-(4-PIPERIDYL)-PROPANOL

This application is a continuation of application Ser. No. 324,713, filed Nov. 24, 1981, now abandoned.

The present invention relates to new medicaments, particularly useful as antiarhythmics, which contain, as active substance, a compound corresponding to the formula:

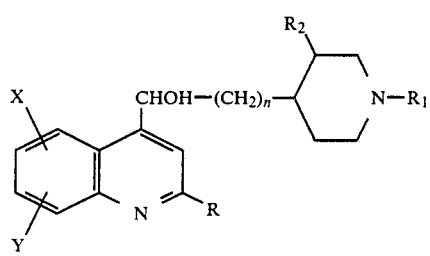

in which n is equal to 1 or 2, X and Y, which are the same or different, are fixed in position 5, 6, 7 or 8 on the quinoline cycle and each represents a hydrogen atom or an alkoxy group having 1 to 3 carbon atoms, R represents a hydrogen atom, a cycloalkyl group having 3 to 8 carbon atoms, an alkyl group having 1 to 4 carbon atoms, a phenyl group or a phenyl group substituted by an alkoxy group having 1 to 4 carbon atoms, $R_1$ represents a hydrogen atom, an alkyl group having 1 to 4 carbon atoms or a phenylalkyl group the alkyl part of which having 1 to 3 carbon atoms, $R_2$ represents a hydrogen atom, an alkyl group having 1 or 2 carbon atoms or an alkenyl group having 2 to 4 carbon atoms, or a mixture of stereoisomeric compounds corresponding to the formula (I), or a salt of such a compound or mixture of stereoisomeric compounds with a pharmaceutically acceptable acid.

In formula (I) above, Y is preferably a hydrogen atom, X is preferably a hydrogen atom or a methoxy group, R is preferably a hydrogen atom or a phenyl or tertiobutyl group, $R_1$ is preferably a hydrogen atom and $R_2$ is preferably a hydrogen atom or an ethyl or ethenyl group.

When $R_2$ represents a hydrogen atom, the molecule of the compounds of formula (I) contains an asymmetric carbon atom (carbon atom carrying the OH group) and then, for a given significance of X, Y, R, $R_1$, $R_2$ and n, there are a racemic compound and two enantiomers corresponding to the plane formula (I). When $R_2$ does not represent a hydrogen atom, the molecule of the compounds of formula (I) contains 3 asymmetric carbon atoms and then, for a given significance of X, Y, R, $R_1$, $R_2$ and n, there are 8 stereoisomers corresponding to the plane formula (I), the spatial formulae of which correspond to the combinations 3 to 3 of the rectus (R) or sinister (S) configurations of each center of asymmetry. The medicaments according to the invention may contain, as active substance, a mixture of stereoisomeric compounds corresponding to formula (I) as well as a pure isomer corresponding to formula (I).

Products are known (cf. M. Heidelberger and W. A. Jacobs, J. Am. Chem. Soc. 44, 1098–1107, (1922); German Pat. No. 330,813) which are probably mixtures of isomers and correspond to the formula:

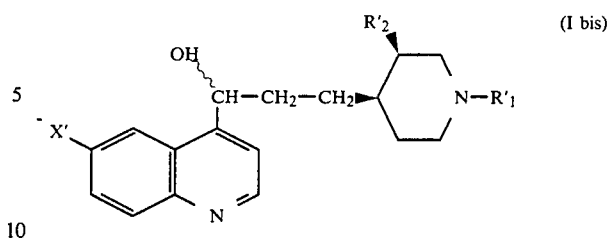

in which X' is a hydrogen atom or a methoxy or ethoxy group, $R'_1$ is a hydrogen atom or a methyl or ethyl group and $R'_2$ is an ethyl or ethenyl group, but no pharmacological property or therapeutic application has been taught or suggested for these products up to the present.

According to G. S. Dawes (Brit. J. Pharmacol., 1946, 1, 90-111), the compound of the formula:

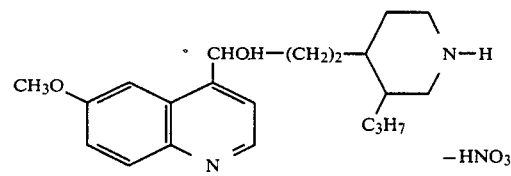

would act on the capacity of the isolated rabbit auricle for responding to electrical stimuli caused by an induction coil, but the molar weight (391) given by the author for the above compound is inconsistent with the formula, so that there is doubt about the true structure of the tested compound.

It has now been found, according to the present invention, that the compounds of formula (I) possess remarkable pharmacological properties which enable them to be used as an active ingredient of medicaments.

The racemic, enantiomeric or stereoisomeric compounds of the formula:

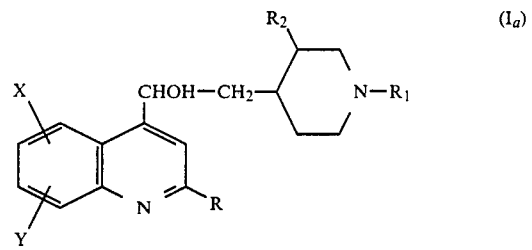

wherein X, Y, R, $R_1$ and $R_2$ have the same significance as in formula (I), are new compounds and as such form a part of the invention.

The racemic, enantiomeric or stereoisomeric compounds of the formula:

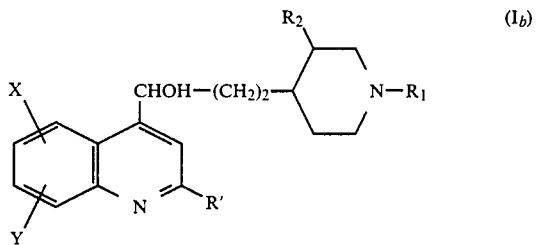

wherein X, Y, R₁ and R₂ have the same significance as in formula (I) and R' represents a cycloalkyl group having 3 to 8 carbon atoms, an alkyl group having 1 to 4 carbon atoms, a phenyl group or a phenyl group substituted with an alkoxy group having 1 to 4 carbon atoms, are new compounds and as such form a part of the invention.

The racemic or enantiomeric compounds of the formula:

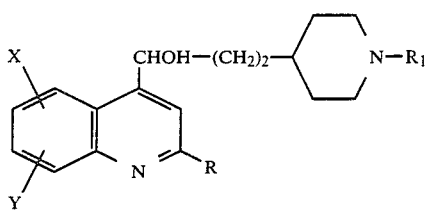

(I_c)

wherein X, Y, R and R₁ have the same significance as in formula (I) are new compounds and as such form a part of the invention.

The compounds of formula (I) can be prepared by reduction of the ketones of the formula:

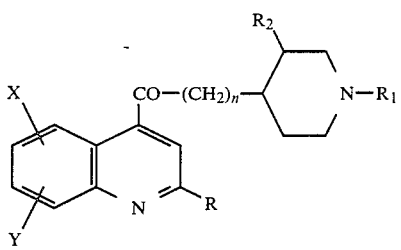

(II)

in which X, Y, R, R₁, R₂ and n have the same significance as in formula (I).

In order to effect this reduction, processes are used known per se, which enable a ketone to be converted into an alcohol. An advantageous method, applicable in all cases, consists in using as reducing agent a reducing metal hydride such as those mentioned in "Complex Hydrides and Related Reducing Agents in Organic Synthesis" (Andor Hajos, Elsevier Scientific Publishing Company, Amsterdam, Oxford, New York, 1979). Among the most common reducing agents may be mentioned the borohydrides of alkali metals such as sodium borohydride and potassium borohydride, which are used at the ambient temperature in a solvent such as an alcohol (for example methanol or ethanol), a water-alcohol mixture or tetrahydrofuran, and lithium aluminum hydride, which is used in an inert solvent such as diethyl ether, tetrahydrofuran or a hydrocarbon, at a temperature between 0° C. and the boiling temperature of the solvent.

When R₂ is a hydrogen atom, reduction of the ketones of formula (II) provides the racemic compound. When R₂ is not a hydrogen atom, reduction of the ketones of formula (II) provides a mixture of diastereoisomeric compounds, which are racemic or optically active accordingly as the starting ketone is racemic or optically active. The pure diastereoisomers can be isolated from the mixture by conventional methods such as chromatography, fractional crystallization, formation of salts and regeneration of the base, etc.

A variant of the above reduction process consists in effecting the reduction in the presence of an optically active compound, capable of forming a complex with the reducing hydride used, for example an α amino-acid [cf. J. B. Morrison and H. S. Mosher, Asymmetric Organic Reactions, Prentice Hall, Englewood Cliffs, N.J. (1972); J. W. Apsimon and R. P. Seguin, Tetrahedron, 1979, 35, 2797; J. C. Fiaud, Stereochemistry Fundamentals and Methods, Vol. 3, 95, edited by H. B. Kagan, Georg Thieme Publishers, Stuttgart, 1977; N. Umino, Chem. Pharm. Bull., 1979, 27, 1479]. Under these conditions a product of reduction is obtained containing in preponderant amount an enantiomer (if R₂=H) or a diastereoisomer (if R₂≠H), the carbon atom of which carrying the OH group having a definite configuration. For example, L-proline induces the preponderant formation of an alcohol in which the carbon atom carrying the OH group has the sinister (S) configuration and D-proline induces the preponderant formation of an alcohol in which the carbon atom carrying the OH group has the rectus (R) configuration. This variant is advantageous in the case where the starting ketone of formula (II) is optically active. A reduction product is then obtained containing essentially a definite diastereoisomer, optically active, which is easily isolated by the methods indicated above.

The compounds of formula (I) for which R₁ does not represent a benzyl group and R₂ represents an alkyl group having 2 carbon atoms can also be prepared by catalytic hydrogenation of the corresponding ketones of formula (II) for which R₂ represents an alkenyl group having 2 carbon atoms. In this case the reduction of the CO group to CHOH and the hydrogenation of the alkenyl group to an alkyl group are effected at the same time. The operation is generally effected in the neighborhood of the ambient temperature, under a pressure of hydrogen near to the atmospheric pressure, the starting ketone (in the form of the free base or one of its salts) being in an inert solvent such as an alcohol (for example methanol or ethanol), a water-alcohol mixture or an acid (for example acetic acid). The catalysts may be palladium, rhodium, ruthenium, platinum and nickel.

The compounds of formula (I) for which R₁ is a hydrogen atom and R₂ is the ethenyl group and for which the carbon atom carrying the ethenyl group has a given configuration, rectus (R) or sinister (S), can also be prepared by heating, at a temperature greater than 50° C., in a protic solvent or a mixture of protic solvents, in the presence of formaldehyde, the corresponding compounds of formula (I) for which R₁ is a hydrogen atom, R₂ is the ethenyl group and the carbon atom carrying the ethenyl group has the sinister configuration (S) or rectus configuration (R), partially or totally in salt form.

The compounds of formula (I) for which R₁ is an alkyl or phenylalkyl group can also be prepared by the action on the corresponding compounds of formula (I) for which R₁ is a hydrogen atom, of an alkylating agent such as a halide of formula R"₁Hal, a sulfate of formula (R"₁)₂SO₄, an arylsulfonate of formula ArSO₃R"₁ or an alkylsulfonate of the formula R"SO₃R"₁, in which formulae R"₁ represents an alkyl group having 1 to 4 carbon atoms or a phenylalkyl group the alkyl part of which contains 1 to 3 carbon atoms, Ar represents an aryl group and R" represents an alkyl group. The reaction can be shown graphically as follows in the case where the alkylating agent is a halide:

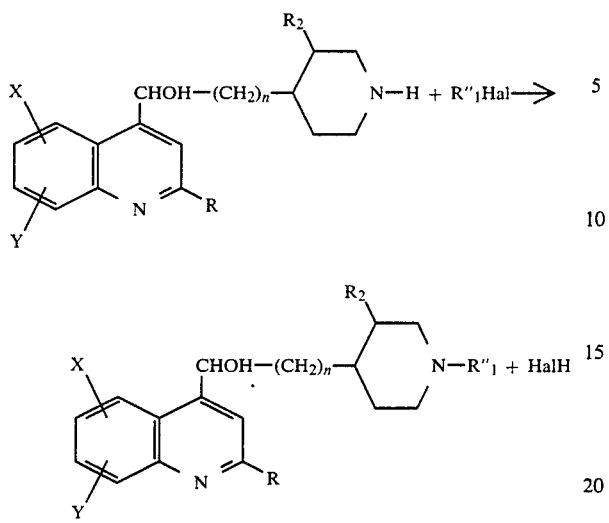

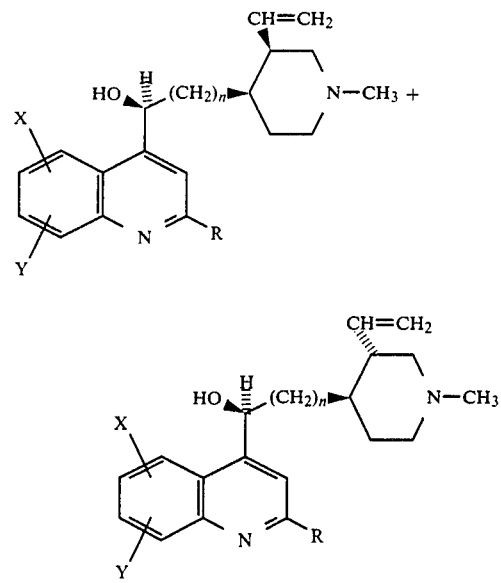

The reaction of the alkylating agent with the compounds of formula (I) for which $R_1=H$ is effected according to processes known per se. The operation is advantageously effected in the presence of an organic or mineral base (for example sodium or potassium carbonate), in an inert solvent, for example dimethylformamide.

An interesting variant for the preparation of the compounds of formula (I) for which $R_1=CH_3$ consists in acting on the corresponding compounds of formula (I) for which $R_1=H$ with formaldehyde in the presence of a reducing agent (Cf. "Complex Hydrides and Related Reducing Agents in Organic Synthesis" above cited). As reducing agent is advantageously used a borohydride such as sodium or potassium borohydride or sodium cyanoborohydride, in an inert solvent, for example an alcohol or a mixture of water and alcohol, at a temperature between the ambient temperature and the boiling point of the solvent.

When $R_2$ represents the ethenyl group and if the operation is effected at a sufficiently high temperature (>50° C.), there is simultaneously observed, during the action of the formaldehyde in the presence of the reducing agent, the epimerization of the ethenyl group, so that in a single reaction there can be prepared, from a single precursor, two diastereoisomers differing from one another by the configuration of the carbon atom carrying the ethenyl group. The reaction may be shown graphically as follows.

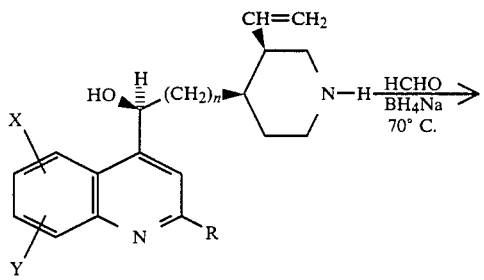

Each diastereoisomer can be isolated in the pure state from the mixture by the methods indicated above.

The compounds of formula (I) in the free base form may, if desired, be converted into salts of addition with a mineral or organic acid by the action of such an acid in a suitable solvent.

Some of the ketones of formula II are known. This is the case in particular of quinicine and cinchonicine, which are obtained by rearrangement in acid medium of the major alkaloids of the cinchona, that is of quinine or quinidine and of cinchonine or cinchonidine (cf. S. W. Pelletier, Chemistry of the Alkaloids, p. 313, Reinhold, 1969), and which correspond to the formula:

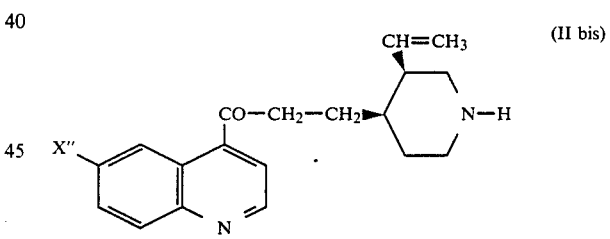

in which X" is a hydrogen atom or a methoxy group.

Generally, the ketones of formula (II) for which $R_1$ represents a hydrogen atom may be prepared by condensation of an ester of quinoline-4-carboxylic acid of formula (III) with an ester of (4-piperidinyl)-alkylcarboxylic acid of formula (IV), then hydrolysis and decarboxylation of the compound of formula (V) thus obtained, according to the following reaction scheme:

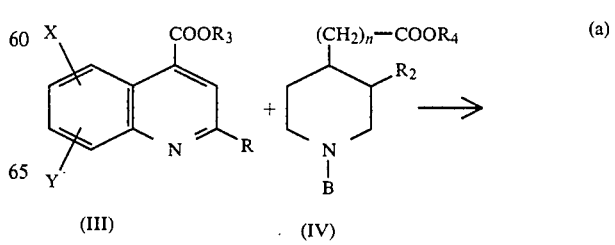

-continued

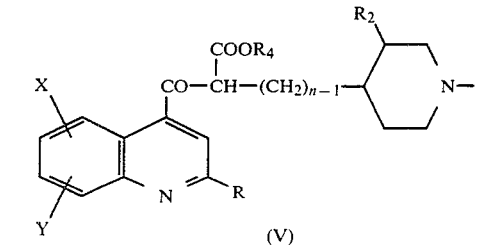

(V) + 2H₂O ⟶ (b)

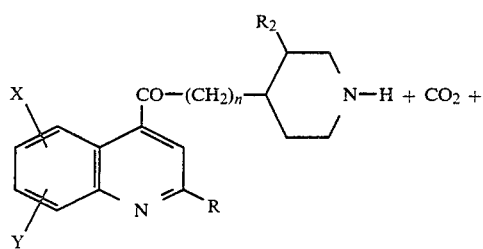

R₄OH + BOH

In formulae (III), (IV) and (V) above, X, Y, R, $R_2$ and n have the same significance as in formula (I), $R_3$ and $R_4$ represent alkyl groups of low molecular weight, for example methyl or ethyl, and B represents a group protecting the amine function, stable in anhydrous alkaline medium and capable of being eliminated in acid medium, such as those which are described by R. A. Boissonnas, Advances in Organic Chemistry 3, p. 159, Interscience (1963). The benzoyl group (—B=—CO—C₆H₅) or the benzyloxycarbonyl group (—B=—CO—O—CH₂—C₆H₅) is advantageously used.

In order to carry out condensation reaction (a) processes known per se are made use of (cf. "The Acetoacetic Acid Ester Condensation", C. R. Hauser and coll., Organic Reactions, vol. 1, p. 266, Wiley and Sons, 1942). The operation is advantageously effected in the presence of a base such as an alcoholate (for example potassium tertiobutylate) or a metal hydride (for example sodium or potassium hydride), in an inert solvent such as a hydrocarbon or another aprotic solvent (for example tetrahydrofuran), at a temperature between 0° C. and the boiling temperature of the solvent used.

The hydrolysis reaction (b) is carried out according to processes known per se (cf. "Cleavage of β Ketoesters", R. B. Wagner and H. D. Zook, Synthetic Organic Chemistry, p. 327, Wiley and Sons, 1953). The most usual method consists in heating the product of formula (V) at the boil in an aqueous solution of an acid such as hydrochloric or sulfuric acid.

The ketones of formula (II) for which $R_1$ does not represent a hydrogen atom may be prepared by the action of an alkylating agent on the ketones of formula (II) for which $R_1$=H. This alkylation is effected under the conditions indicated above for the alkylation of the compounds of formula (I) for which $R_1$=H.

The following examples illustrate the preparation of the compounds of formula (I), which are the active substances of the medicaments according to the invention. In these examples, the absolute configuration of the carbon atom which carries the OH group of the synthesized compounds has been determined by the method of J. A. Dale and H. S. Mosher, J. Amer. Chem. Soc., 1973, 95, 512.

EXAMPLE 1

1-(2-PHENYL-4-QUINOLYL)-2-(4-PIPERIDYL)-ETHANOL (racemic)

6 g of sodium borohydride were added in 20 minutes, at the ambient temperature, to 16 g of 1-(2-phenyl-4-quinolyl)-2-(4-piperidyl)-ethanone dihydrochloride in 500 ml of methanol. After reacting for 2 hours at the ambient temperature, 350 ml of water were added and the methanol was removed by distillation under reduced pressure. The residual aqueous suspension was extracted with diethyl oxide, the organic phase was washed with water, dried over magnesium sulfate and evaporated under reduced pressure. The residue (13 g) was crystallized from petrol ether. 9 g of 1-(2-phenyl-4-quinolyl)-2-(4-piperidyl)-ethanol (racemic) were thus obtained, which melted at 147° C.

The starting product may be prepared as follows:

A solution of 21.2 g of methyl(2-phenyl-quinoline)-4-carboxylate in 50 ml of dry tetrahydrofuran was rapidly added to a suspension of 27.5 g of potassium t-butylate in 215 ml of dry tetrahydrofuran, placed under an atmosphere of nitrogen and cooled to 0° C. While maintaining the temperature below +10° C., a solution of 22.1 g of ethyl(1-benzoyl-4-piperidyl)-acetate in 80 ml of dry tetrahydrofuran was introduced slowly over a period of 2 hours. The reaction mixture was then stirred for 20 hours at the ambient temperature, and then was brought to dryness by evaporation of the solvent. The residue was heated under reflux for 18 hours in 650 ml of a 5N aqueous solution of hydrochloric acid.

After cooling, the solution obtained was filtered and the filtrate extracted twice by 250 ml of diethyl ether each time. The residual aqueous solution was concentrated under reduced pressure. The residue obtained was extracted by 500 ml of hot methanol and the extraction solution was filtered. The filtrate, after evaporation of the methanol, provided 13.8 g of 1-(2-phenyl-4-quinolyl)-2-(4-piperidyl)-ethanone dihydrochloride melting at 259° C.

EXAMPLE 2

1-(4-QUINOLYL)-3-(4-PIPERIDYL)-1-PROPANOL (racemic)

2 g of sodium borohydride were added in 20 minutes, at the ambient temperature, to 13 g of 1-(4-quinolyl)-3-(4-piperidyl)-1-propanone in 200 ml of methanol. After reacting for 2 hours at the ambient temperature, the reaction medium was acidified by addition of an aqueous solution of hydrochloric acid, the methanol removed by distillation under reduced pressure and the aqueous phase washed with ethyl acetate. The aqueous phase was made alkaline by addition of an aqueous solution of sodium hydroxide, then extracted with chloroform. The chloroformic phase was washed with water, dried over magnesium sulfate and evaporated under reduced pressure. 13 g of crude product were thus obtained, which were fixed on a column of silica gel. It was then eluted with a mixture of 90 parts by volume of chloroform and 10 parts by volume of diethylamine. 7 g of the desired product were thus isolated in the form of the base, which was converted into dihydrochloride by the action of hydrochloric acid in ethanol. 3.2 g of 1-(4-quinolyl)-3-(4-piperidyl)-1-propanol dihydrochloride (racemic) which melted at 195° C. were thus obtained.

The starting ketone can be prepared as indicated by P. Rabe, Ber., 55, 532 (1922).

EXAMPLE 3

1-(6-METHOXY-4-QUINOLYL)-3-(4-PIPERIDYL)-1-PROPANOL (racemic)

The operation was as in Example 2, except that 6.6 g of 1-(6-methoxy-4-quinolyl)-3-(4-piperidyl)-1-propanone and 1 g of sodium borohydride in 100 ml of methanol were used and that the product desired in the form of the base was converted into its sesquifumarate. 5 g of 1-(6-methoxy-4-quinolyl)-3-(4-piperidyl)-1-propanol sesquifumarate (racemic) were thus obtained which melted at 154° C.

The starting ketone was prepared as indicated by M. Kleiman J. Org. Chem., 1945, 10, 562.

EXAMPLE 4

1-(2-PHENYL-4-QUINOLYL)-3-(4-PIPERIDYL)-1-PROPANOL (racemic)

The operation was as in Example 1, except that 14 g of 1-(2-phenyl-4-quinolyl)-3-(4-piperidyl)-1-propanone and 2.3 g of sodium borohydride in 300 ml of methanol were used. After recrystallization of the crude product in isopropanol, 7 g of 1-(2-phenyl-4-quinolyl)-3-(4-piperidyl)-1-propanol (racemic) were obtained, which melted at 162° C.

The starting ketone can be prepared as indicated in Belgian Pat. No. 807,491.

EXAMPLE 5

Mixture of 3-[3(R)-ETHENYL 4(R)-PIPERIDYL]-1-(6-METHOXY-4-QUINOLYL)-1-(R)-PROPANOL and 3-[3(R)-ETHENYL 4(R)-PIPERIDYL]-1-(6-METHOXY-4-QUINOLYL)-1(S)-PROPANOL 26.6 g of sodium borohydride were added to 194 g of 3-[3(R)-ethenyl 4(R)-piperidyl]-1-(6-methoxy-4-quinolyl)-1-propanone monohydrochloride and 32 g of sodium methylate in 2200 ml of methanol. After 2 hours stirring at the ambient temperature, the reaction mixture was filtered and the methanol evaporated under reduced pressure. The residue was taken up with 1 liter of methylene chloride and 500 ml of water and extracted, the phases were separated and the aqueous phase extracted again with 500 ml of methylene chloride.

The organic phases collected were washed three times with 200 ml of water each time, dried over magnesium sulfate and evaporated under reduced pressure. The residual oil was dissolved in 500 ml of absolute ethanol and the medium brought to pH≃3 by addition of a 10N solution of hydrochloric acid in ethanol. The crystals formed were filtered, washed and dried. 144 g of a mixture of 3-[3(R)-ethenyl 4(R)-piperidyl]-1-(6-methoxy-4-quinolyl)-1(R)-propanol and 3-[3(R)-ethenyl 4(R)-piperidyl]-1-(6-methoxy-4-quinolyl)-1(S)-propanol in the form of dihydrochlorides were thus obtained. This mixture melted at 223°-225° C. Analysis by high pressure liquid chromatography of this mixture showed that it consisted in a 50/50 mixture of the two diastereoisomers.

The starting ketone (quinicine hydrochloride) may be prepared as indicated by A. Quevauviller et al., Ann. Pharm. Franc. 24, 39 (1966).

EXAMPLE 6

3-[3(R)-ETHENYL 4(R)-PIPERIDYL]-1-(6-METHOXY-4-QUINOLYL)-1(S)-PROPANOL

The product obtained in Example 5 was recrystallized three times from 95% ethanol. 18 g of 3[3(R)-ethenyl 4(R)-piperidyl]-1-(6-methoxy-4-quinolyl)-1(S)-propanol were thus obtained, in the form of the dihydrochloride melting at 245°-248° C. Rotatory power of the product obtained (measured on a 2% aqueous solution):

$$\alpha_D^{21} = -122°8$$

EXAMPLE 7

3-[3(R)-ETHENYL 4(R)-PIPERIDYL]-1-(6-METHOXY-4-QUINOLYL)-1(R)-PROPANOL

The filtrate from the first recrystallization effected in Example 6 was evaporated. The residue was recrystallized once in isopropanol, then three times in a 1/1 absolute ethanol-isopropanol mixture. 8 g of 3-[3(R)-ethenyl 4(R)-piperidyl]-1-(6-methoxy-4-quinolyl)-1(R)-propanol were thus obtained in the form of the dihydrochloride which melted at 220°-222° C. The rotatory power of the product obtained (measured on a 2% aqueous solution) was:

$$\alpha_D^{21} = +197°9$$

EXAMPLE 8

3-[3(R)-ETHYL 4(R)-PIPERIDYL]-1-(6-METHOXY-4-QUINOLYL)-1(S)-PROPANOL and 3-[3(R)-ETHYL 4(R)-PIPERIDYL]-1-(6-METHOXY-4-QUINOLYL)-1(R)-PROPANOL Hydrogenation was effected at the ambient temperature, under a pressure of hydrogen equal to the atmospheric pressure and in the presence of 23 g of palladium in the form of palladium charcoal with 10% of palladium, on 180 g of 3-[3(R)-ethenyl 4(R)-piperidyl]-1-(6-methoxy-4-quinolyl)-1-propanone monohydrochloride in 2250 ml of absolute ethanol and 250 ml of a 2N aqueous solution of hydrochloric acid. When the absorption of hydrogen was completed, the reaction mixture was filtered and then evaporated under reduced pressure. The residual oil was taken up with 500 ml of hot ethanol, and 500 ml of acetone were added in order to start the crystallization. The crystals formed were filtered, washed and dried. 143 g of a crude product were thus obtained, which was a mixture of equal parts of the dihydrochlorides of 3-[3(R)-ethyl 4(R)-piperidyl]-1-(6-methoxy-4-quinolyl-1(S)-propanol and 3-[3(R)-ethyl 4(R)-piperidyl]-1-(6-methoxy-4-quinolyl)-1(R)-propanol.

The above crude product was recrystallized three times in 95% ethanol and the dihydrochloride crystals thus isolated were converted into the corresponding base by the action of sodium hydroxide. This base was fixed on a column of silica gel and then eluted with a mixture containing 1 part by volume of chloroform, 0.1 part by volume of methanol and 0.025 part by volume of diethylamine. 11.3 g of product were thus obtained in the form of the base, which was converted into the dihydrochloride by the action of hydrochloric acid in absolute ethanol. After a recrystallization of this dihydrochloride in absolute ethanol, 7 g of 3-[3(R)-ethyl 4(R)-piperidyl]-1-(6-methoxy-4-quinolyl)-1(S)-propanol dihydrochloride were isolated. This product melted at 228°–230° C. and its rotatory power, measured on a 2% aqueous solution, was:

$$\alpha_D{}^{21} = -144°2$$

The filtrate (about 1300 ml) coming from the first recrystallization of the crude product in 95% ethanol was concentrated until its volume was reduced by half. The solution obtained was filtered and the filtrate concentrated again until its volume was reduced by half. The solution obtained was filtered again, and the residual filtrate was evaporated to dryness under reduced pressure. 29 g were thus obtained of product in the form of the dihydrochloride, which was converted into the corresponding base by the action of sodium hydroxide. This base was fixed on a column of silica gel and then eluted with a 1/0.1/0.025 chloroform-methanol-diethylamine mixture. The product thus isolated in the form of the base was converted into the dihydrochloride by the action of HCl in absolute ethanol. The dihydrochloride was then recrystallized in n-propanol. 5 g were thus obtained of 3-[3(R)-ethyl 4(R)-piperidyl]-1-(6-methoxy-4-quinolyl)-1(R)-propanol dihydrochloride, which melted at 210°–215° C. The rotatory power of this product measured on a 2% aqueous solution, was:

$$\alpha_D{}^{21} = +157°4$$

EXAMPLE 9

3-[3(R)-ETHENYL 1-METHYL 4(R)-PIPERIDYL]-1-(6-METHOXY-4-QUINOLYL)-1(S)-PROPANOL and 3-[3(S)-ETHENYL 1-METHYL 4(R)-PIPERIDYL]-1-(6-METHOXY-4-QUINOLYL)-1(S)-PROPANOL 8 g of 3-[3(R)-ethenyl 4(R)-piperidyl]-1-(6-methoxy-4-quinolyl)-1(S)-propanol (product of Example 6) were treated for 2 hours, at 70° C., with 24 ml of a 37% aqueous solution of formaldehyde and 3.4 g of sodium borohydride in 100 ml of methanol. The solvent was evaporated under reduced pressure, the residue was taken up with water, the aqueous phase was made alkaline and extracted with chloroform. The organic phase was washed with water, dried over magnesium sulfate and evaporated under reduced pressure.

The residue was subjected to high pressure liquid chromatography (support: silica; eluant; mixture of 9 parts by volume of toluene and 1 part by volume of diethylamine). The desired products, which were in the form of the base in the separated fractions, were converted into hydrochlorides by the action of HCl in ethanol. There were thus obtained on the one hand 2.5 g of 3-[3(R)-ethenyl 1-methyl-4(R)-piperidyl]1-(6-methoxy-4-quinolyl)-1(S)-propanol in the form of the monohydrochloride, which melted at 214° C. and had a rotatory power (measured on a 2% aqueous solution) of:

$$\alpha_D{}^{23} = -61°9$$

and on the other hand 2.7 g of 3-[3(S)-ethenyl 1-methyl-4(R)-piperidyl]-1-(6-methoxy-4-quinolyl)-1(S)-propanol in the form of the dihydrochloride, which melted at 175° C. and had a rotatory power (measured on a 2% aqueous solution) of:

$$\alpha_D{}^{22} = -172°8$$

EXAMPLE 10

3-[3(R)-ETHENYL 1-METHYL 4(R)-PIPERIDYL]-1-(6-METHOXY-4-QUINOLYL)-1(R)-PROPANOL

The operation was as in Example 9, starting from 1.15 g of 3-[3(R)-ethenyl 4(R)-piperidyl]-1-(6-methoxy-4-quinolyl)-1(R)-propanol (product of Example 7), 3.5 ml of 37% aqueous solution of formaldehyde and 0.5 g of sodium borohydride in 15 ml of methanol. After separation by high pressure liquid chromatography, 0.6 g were isolated of 3-[3(R)-ethenyl 1-methyl 4(R)-piperidyl]-1-(6-methoxy-4-quinolyl)-1(R)-propanol in the form of the monohydrochloride, which melted at 160°–165° C. and had a rotatory power (measured on a 2% aqueous solution) of:

$$\alpha_D{}^{23} = +199°0$$

EXAMPLE 11

Mixture of the two isomers 3-[3(R)-ETHENYL 4(R)-PIPERIDYL]-1-(6-METHOXY-4-QUINOLYL)-1(R)-PROPANOL and 3-[3(R)-ETHENYL 4(R)-PIPERIDYL]-1-(6-METHOXY-4-QUINOLYL)-1(S)-PROPANOL 0.095 g of sodium borohydride and 0.29 g of L-proline in 5 ml of dry tetrahydrofuran were stirred for 20 hours at the ambient temperature. Then 0.9 g of 3-[3(R)-ethenyl 4(R)-piperidyl]-1-(6-methoxy-4-quinolyl)-1-propanone monohydrochloride was added and stirring of the reaction mixture was continued for 4 days. The solvent was evaporated under reduced pressure, the residue was taken up with water, the aqueous phase was made alkaline and extracted with methylene chloride. The organic phase was dried over magnesium sulfate and evaporated under reduced pressure. 0.8 g of an oil were obtained which, subjected to the action of HCl in ethanol, provided 0.4 g of a mixture of the dihydrochlorides of 3-[3(R)-ethenyl 4(R)-piperidyl]-1-(6-methoxy-4-quinolyl)-1(R)-propanol and 3-[3(R)-ethenyl 4(R)-piperidyl]-1-(6-methoxy-4-quinolyl)1(S)-propanol. This mixture melted at 223°–225° C. and contained 90% of isomer 3R, 4R, 1S and 10% of isomer 3R, 4R, 1R, as shown by analysis by high pressure liquid chromatography of the corresponding mixture of the bases.

EXAMPLE 12

1-[2-(1,1-DIMETHYL-ETHYL)-4-QUINOLYL]-3-(4-PIPERIDYL)-1-PROPANOL (racemic)

The operation was as in Example 5, starting from 14 g of the dihydrochloride of 1-[2-(1,1-dimethyl-ethyl)-4-quinolyl]-3-(4-piperidyl)-1-propanone, 4.15 g of sodium methylate and 1.8 g of sodium borohydride in 150 ml of methanol. 4.1 g were finally obtained of 1-[2-(1,1-dimethyl-ethyl)-4-quinolyl]-3-(4-piperidyl)-1-propanol (racemic), in the form of the dihydrochloride melting at 219° C.

The starting ketone can be prepared in the following way:

29.6 g of an 80% suspension of sodium hydride in oil were added to a solution of 48 g of ethyl[2-(1,1-dimethyl-ethyl)-quinoline]-4-carboxylate in 800 ml of anhydrous tetrahydrofuran, placed in an atmosphere of nitrogen. The mixture was brought to the boil and, in 2 hours, there was added a solution of 47 g of ethyl 3-(1-benzoyl-4-piperidyl)-propionate in 100 ml of anhydrous tetrahydrofuran. Boiling was then maintained for 2 hours. After cooling, 100 ml of ethanol were added, and the mixture was evaporated to dryness. The residue was taken up with water and the aqueous solution brought to pH 6 by addition of acetic acid. The insoluble material was extracted 3 times with 300 ml of ethyl acetate each time, the organic phase was washed with water, dried over magnesium sulfate and evaporated under reduced pressure. The residue (36 g) was heated under reflux for 19 hours in 500 ml of a 5N aqueous solution of hydrochloric acid. The aqueous solution was made alkaline by addition of a sodium hydroxide lye, the insoluble material was extracted 3 times with 300 ml of chloroform each time, the organic phase was washed with water, dried over magnesium sulfate and evaporated under reduced pressure. 35 g of crude product were thus obtained which, when subjected to the action of hydrochloric acid in ethanol, provided 28 g of 1-[(2-(1,1-dimethyl-ethyl)-4-quinolyl]-3-(4-piperidyl)-1-propanone, in the form of the dihydrochloride melting at 200° C.

The ethyl[2-(1,1-dimethyl-ethyl)-quinoline]-4-carboxylate may be prepared as indicated by J. P. Schaefer et al. (J. Heterocycl. Chemistry, 1970, 607).

EXAMPLE 13

1-[2-(1,1-DIMETHYL-ETHYL)-4-QUINOLYL]-3-[1-(2-PHENYL-ETHYL)-4-PIPERIDYL]-1-PROPANOL (racemic)

The operation was as in Example 5, starting from 10 g of 1-[2-(1,1-dimethyl-ethyl)-4-quinolyl]-3-[1-(2-phenyl-ethyl)-4-piperidyl]-1-propanone dihydrochloride, 2.2 g of sodium methylate and 0.8 g of sodium borohydride in 250 ml of methanol. 8.4 g of 1-[2-(1,1-dimethyl-ethyl)-4-quinolyl]-3-[1-(2-phenyl-ethyl)-4-piperidyl]-1-propanol dihydrochloride (racemic), which melted at 190° C. were obtained.

The starting ketone may be prepared in the following way:

A mixture of 14 g of 1-[2-(1,1-dimethyl-ethyl)-4-quinolyl]-3-(4-piperidyl)-1-propanone dihydrochloride, 9 g of (2-phenyl-ethyl)bromide and 21.3 g of potassium carbonate in 140 ml of dimethylformamide was heated for 7 hours at 70° C. The dimethylformamide was then eliminated by distillation under reduced pressure and the residue taken up with 400 ml of water and 200 ml of toluene. The organic phase was separated, washed with 200 ml of water, dried and evaporated under reduced pressure. The crude product thus obtained, when subjected to the action of hydrochloric acid in ethanol, provided 13.7 g of 1-[2-(1,1-dimethyl-ethyl)-4-quinolyl]-3-]1-(2-phenyl-ethyl)-4-piperidyl]-1-propanone dihydrichloride, which melted at 130° C.

EXAMPLE 14

2-[1-METHYL-4-PIPERIDYL)-1-(2-PHENYL-4-QUINOLYL)-ETHANOL (racemic)

A mixture of 2.55 g of 1-(2-phenyl-4-quinolyl)-2-(4-piperidyl)-ethanol (racemic), 1.1 g of methyl iodide and 0.6 g of potassium carbonate in 20 ml of dimethylformamide was stirred for 2 hours at the ambient temperature. 20 ml of water and 30 ml of toluene were then added. The organic phase was separated, wahsed with water, dried over magnesium sulfate and evaporated under reduced pressure. 1 g of crude product was obtained which was fixed on a column of silica gel. The elution was effected with a 9/1 chloroform-diethylamine mixture. 0.57 g of 2-(1-methyl-4-piperidyl)-1-(2-phenyl-4-quinolyl)-ethanol (racemic), which melted at 208° C. was thus isolated.

EXAMPLE 15

3-[3(S)-ETHYL 4(R)-PIPERIDYL]-1-(6-METHOXY-4-QUINOLYL)-1(S)-PROPANOL

A mixture of 6 g of 3-[3(R)-ethenyl 4(R)-piperidyl]-1-(6-methoxy-4-quinolyl)-1(S)-propanol dihydrochloride, 15 ml of a normal aqueous solution of sodium hydroxide, 1.2 ml of a 0.4% aqueous solution of formaldehyde and 60 ml of water was heated at 120° C. for 24 hours in an autoclave. After cooling, the reaction medium was made alkaline by addition of sodium hydroxide lye and extracted with methylene chloride. The organic phase was washed with water, dried over magnesium sulfate and evaporated under reduced pressure. The oily residue obtained was subjected to high pressure liquid chromatography (support: silica gel; eluant: 100/7.5/3.75 toluene-methanol-diethylamine mixture). The separated fractions containing the desired product were evaporated. There was thus recovered 2.6 g of an oil which, by the action of HCl in ethanol, was converted into the dihydrochloride. After three recrystallizations of this last product in ethanol, 0.7 g of 3-[3(S)-ethenyl 4(R)-piperidyl]-1-(6-methoxy-4-quinolyl)-1(S)-propanol were obtained in the form of the dihydrochloride melting at 204° C.

EXAMPLE 16

1-(2-CYCLOHEXYL-4-QUINOLYL)-3-(4-PIPERIDYL)-1-PROPANOL (racemic)

The operation was as in Example 5, starting from 5.1 g of 1-(2-cyclohexyl-4-quinolyl)-3-(4-piperidyl)-1-propanone monohydrochloride, 1.3 ml of a 10N aqueous solution of sodium hydroxide (instead of sodium methylate) and 0.53 g of sodium borohydride in 100 ml of ethanol. 1.3 g of 1-(2-cyclohexyl-4-quinolyl)-3-(4-piperidyl)-1-propanol (racemic) were finally obtained in the form of the sulfate melting at 260° C.

The starting ketone may be prepared as follows:

350 ml of anhydrous tetrahydrofuran and 27 g of ethyl (2-cyclohexyl-quinoline)-4-carboxylate were added to 15 g of an 80% suspension of sodium hydride in oil, placed under a nitrogen atmosphere. The mixture was brought to the boil, then a solution of 24 g of ethyl 3-(1-benzoyl-4-piperidyl)-propionate in 100 ml of anhydrous tetrahydrofuran and 12 g of potassium ethylate in 45 ml of dimethylformamide were added. Boiling was maintained for one hour, then the reaction mixture was cooled and 50 ml of ethanol were added. The solvents were eliminated by distillation under reduced pressure, water was added and the pH of the solution brought to 6 by addition of acetic acid. The solution was extracted with ethyl acetate. The organic phase was washed with water, dried over anhydrous magnesium sulfate and evaporated to dryness under reduction pressure. The residue was taken up with 500 ml of a concentrated aqueous solution of hydrochloric acid and the mixture heated at the boiling temperature for 23 hours. After cooling, the solution was made alkaline by addition of a 10N aqueous solution of sodium hydroxide, then the insoluble matter was extracted with methylene chloride. The organic phase was washed with water, dried over anhydrous magnesium sulfate and evaporated to dryness under reduced pressure. The residue was fixed on a column of silica gel, then eluted with a 95/5 chloroform-diethylamine mixture. 14 g of the desired product were thus obtained in the form of the free base, which was then transformed into its monohydrochloride by the action of hydrochloric acid in ethanol. After recrystallization of said monohydrochloride in ethanol, 6.5 g of 1-(2-cyclohexyl-4-quinolyl)-3-(4-piperidyl)-1-propanone monohydrochloride, which melted at 190°–191° C., were isolated.

The ethyl (2-cyclohexyl-quinoline)-4-carboxylate may be prepared according to the method of J. F. Mead et al., J. Am. Chem. Soc., 1946, 68, 2708.

Pharmacological properties of the compounds of formula (I):

The antiarhythmic activity of the compounds of formula (I) has been demonstrated by means of two tests: the aconitine test on the rat and the chloroform test on the mouse.

Aconitine test

The principle of the method rests on the induction time of the ventricular arhythmia caused by the aconitine which is slowly fed by perfusion into rats. An antiarhythmic substance retards the appearance of the arhythmia and the delay is proportional to the activity of the substance.

Groups of 5 male rats were used. An individual anesthesia was effected (10% urethane: 1 g/kg/ip) in order to permit a catheterization of the vein of the penis. The electrocardiogram was recorded. At time T=0 the substance studied was injected in the form of an aqueous solution, at the rate of 2.5 ml of solution per kg in 30 seconds. At time T=60 seconds, say 30 seconds after the end of the injection, the aconitine was perfused at the rate of 20 μg per minute up to the appearance of supraventricular extra systoles. The time of perfusion of the aconitine was noted.

The results are expressed by an $ED_{50}$, which is the dose of product, in mg/kg, increasing by 50% the time of perfusion of the aconitine in comparison with the perfusion time of aconitine for the control animals.

Chloroform test

The technique of Lawson (J. Pharm. Exp. Therap., 160, 2231, 1968) was used, which consists in looking for a possible protection against the fibrillations caused by an inhalation of chloroform, which was continued up to apnoea. The product to be tested was administered intraperitoneally 20 minutes before chloroformic intoxication and the possible protection against the arhythmia was shown by recording of the electrocardiogram, which was effected from the appearance of the apnoea. The activity of the products is expressed by an $AD_{50}$ (dose of product in mg/kg which protects 50% of the animals).

The results obtained are collected in the following Table, where are also given the toxicological data.

TABLE

| Product of Example | Acute toxicity to mice i.v. $LD_{50}$ mg/kg | Antiarhythmic activity | |
|---|---|---|---|
| | | Aconitine test on the rat $ED_{50}$ mg/kg | Chloroform test on the mouse, $AD_{50}$ mg/kg |
| 4 | 21 | 1.22 | 2.5 |
| 5 | 21.5 | 0.44 | 3 |
| 6 | 20.3 | 0.43 | 3 |
| 7 | 33 | 0.45 | 3 |
| 8 (1(S)-propanol isomer) | 17 | 0.58 | 2.5 |
| 8 (1(R)-propanol isomer) | 29 | 0.65 | 2.5 |
| 9 (3(R)-ethenyl isomer) | 19 | 1 | 5 |
| 9 (3(S)-ethenyl isomer) | 33 | 1.4 | >5 |
| 12 | 26 | 0.8 | — |
| Quinidine sulfate (product of reference) | 60 | 7.5 | 18 |

It is seen from the above table that the compounds of formula (I) show remarkable antiarhythmic properties and are more active than the quinidine.

Toxicological properties of the compounds of formula (I):

The acute toxicities of the compounds of formula (I) (see results in the above Table) have been determined on the male mouse $DC_1$ (Charles River), by the intravenous method. The $LD_{50}$ have been calculated, after 3 days observation, by the cumulative method of J. J. Reed and H. Muench (Amer. J. Hyg., 27, 493, 1938).

Therapeutic utilization:

The medicaments according to the invention which contain a compound of formula (I) or a mixture of stereoisomeric compounds corresponding to the formula (I) or a salt of such a compound or mixture of stereoisomeric compounds with a pharmaceutically acceptable acid, associated with a pharmaceutically acceptable vehicle, may be used in human therapeutics for the treatment and/or the prevention of rhythm disturbances. They may be presented in all the forms used in the medicament field, such as compressed tablets, capsules, gelatin-coated pills, suppositories, ingestable or injectable solutions, etc.

The dosage or posology depends on the desired effects and the method of administration used. For example, taken orally, it can be between 50 and 800 mg of active substance per 24 hours, with single doses ranging from 10 to 100 mg of active substance.

What is claimed is:

1. Medicaments useful as antiarrhythmics containing an active substance and a pharmaceutically acceptable vehicle, in which the active substance is (1) a compound corresponding to the formula:

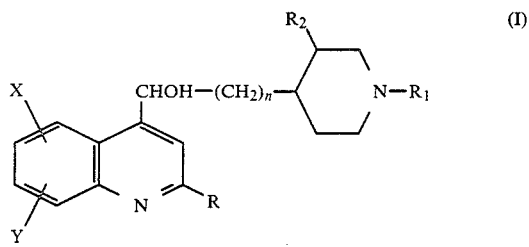

wherein (a) X and Y, which are the same or different, are fixed in position 5, 6, 7 or 8 on the quinoline ring and each represents hydrogen or alkoxy having 1 to 3 carbon atoms, R represents alkyl having 1 to 4 carbon atoms, and $R_1$ and $R_2$ represent hydrogen; or (b) X and Y, which are the same or different, are fixed in position 5, 6, 7 or 8 on the quinoline ring and each represents hydrogen or alkoxy having 1 to 3 carbon atoms, R and $R_1$ represent hydrogen and $R_2$ represents alkyl having 1 to 2 carbon atoms or alkenyl having 2 to 4 atoms or (2) a mixture of stereoisomeric compounds corresponding to formula (I) or (3) a salt of said compound with a pharmaceutically acceptable acid or (4) a mixture of stereoisomeric compounds with a pharmaceutically acceptable acid.

2. Medicaments according to claim 1 in which, in formula (I), Y is hydrogen, X is hydrogen or methoxy, R is tertiobutyl or hydrogen, $R_1$ is hydrogen and $R_2$ is hydrogen, ethyl or ethenyl.

3. Medicaments according to claim 2 in which the active substance is a mixture of 3-[3(R)ethenyl4(R)-piperidyl]-1-(6-methoxy-4-quinolyl)-1(R)-propanol and 3-[3-(R)-ethenyl4(R)-piperidyl]-1-(6-methoxy-4-quinolyl)-1(S)-propanol or a salt of said mixture with a pharmaceutically acceptable acid.

4. Medicaments according to claim 2 in which the active substance is 3-[3(R)-ethenyl 4(R)-piperidyl]-1-(6-methoxy-4-quinolyl)-1(S)-propanol or a salt of said compound with a pharmaceutically acceptable acid.

5. Medicaments according to claim 2 in which the active substance is 3-[3(R)-ethenyl 4(R)-piperidyl]-1-(6-methoxy-4-quinolyl)-1(R)-propanol or a salt of said compound with a pharmaceutically acceptable acid.

6. Medicaments according to claim 2 in which the active substance is 1-[2-(1,1-dimethyl-ethyl)-4-quinolyl]-3-(4-piperidyl)-1-propanol (racemic) or a salt of said product with a pharmaceutically acceptable acid.

7. Medicaments according to claim 2 in which the active substance is 3][3(R)-ethyl 4(R)-piperidyl]-1-(6-methoxy-4-quinolyl)-1(S)-propanol or a salt of said compound with a pharmaceutically acceptable acid.

8. Medicaments according to claim 2 in which the active substance is 3-[3(R)-ethyl 4(R)-piperidyl]-1-(6-methoxy-4-quinolyl)-1(R)-propanol or a salt of said compound with a pharmaceutically acceptable acid.

9. Medicaments according to claim 8 in the form of single doses containing 10 to 100 mg of active substance.

10. Medicaments according to claim 7 in the form of single doses containing 10 to 100 mg of active substance.

11. Medicaments according to claim 6 in the form of single doses containing 10 to 100 mg of active substance.

12. Medicaments according to claim 5 in the form of single doses containing 10 to 100 mg of active substance.

13. Medicaments according to claim 4 in the form of single doses containing 10 to 100 mg of active substance.

14. Medicaments according to claim 3 in the form of single doses containing 10 to 100 mg of active substance.

15. Medicaments according to claim 2 in the form of single doses containing 10 to 100 mg of active substance.

16. Medicaments according to claim 1 in the form of single doses containing 10 to 100 mg of active substance.

17. The racemic, enantiomeric or stereoisomeric compounds of formula:

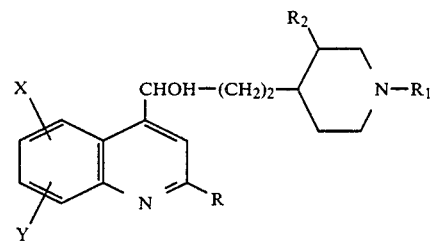

in which X and Y, which are the same or different, are fixed in position 5, 6, 7 or 8 on the quinoline ring and each represents hydrogen or alkoxy having 1 to 3 carbon atoms, R represents alkyl having 1 to 4 carbon atoms, and $R_1$ and $R_2$ represent hydrogen.

18. Compounds according to claim 17 wherein Y is hydrogen, X is hydrogen or methoxy, R is tertiobutyl, $R_1$ is hydrogen and $R_2$ is hydrogen.

19. The compound 1-[2-(1,1-dimethyl-ethyl)-4-quinolyl]-3-(4-piperidyl)-1-propanol (racemic).

20. A process for the treatment or prevention of arrhythmia in a human which comprises orally administering to said human a medicament according to claim 1, the dose of active substance administered being from 50 to 800 mg per 24 hours.

21. A process for the treatment or prevention of arrhythmia in a human which comprises orally administering to said human a medicament according to claim 2, the dose of active substance administered being from 50 to 800 mg per 24 hours.

* * * * *